United States Patent [19]

Fukawa et al.

[11] Patent Number: 5,627,288
[45] Date of Patent: May 6, 1997

[54] METHOD FOR PRODUCING ROSEFURAN PRECURSOR AND INTERMEDIATES THEREFOR

[75] Inventors: Hidemichi Fukawa; Masamichi Nishitani; Mitsuo Chiba; Ruriko Murakami, all of Tokyo, Japan

[73] Assignee: Toyotama Perfumery Co., Ltd., Tokyo, Japan

[21] Appl. No.: 613,868

[22] Filed: Mar. 11, 1996

[30] Foreign Application Priority Data

Aug. 24, 1995 [JP] Japan .................... 7-237916

[51] Int. Cl.$^6$ .................................. C07D 307/88
[52] U.S. Cl. .................... 549/326; 560/174; 562/577
[58] Field of Search .................... 560/174; 562/577; 549/326

[56] References Cited

U.S. PATENT DOCUMENTS

| 3,819,733 | 6/1974 | Ramsden | 562/577 |
| 4,853,473 | 8/1989 | Fischer et al. | 549/326 |

OTHER PUBLICATIONS

Tetrahedron Letters No. 50, pp. 4443–4446, 1977. "Prenylations of But–2–Enolides: Synthesis of Rosefuran and Related Natural Furans", David R. Gedge and Gerald Pattendam.

Chemistry Letters, pp. 1791–1794, 1983. "Highly Chemoselective Synthesis of Ketones From Carboxylic Acids and . . . " Tamotsu Fujisawa et al.

*Primary Examiner*—James H. Reamer
*Attorney, Agent, or Firm*—Keck, Mahin & Cate

[57] ABSTRACT

Disclosed are 3,7-dimethyl-4-oxo-7-octenoic acid and its alkyl esters which are intermediates for producing a fragrance, rosefuran and which are represented by:

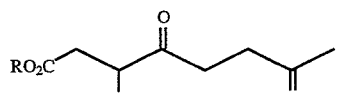

where R is H or a lower alkyl. The compounds [1] are obtained by reacting 2-methyl-3-alkoxycarbonylpropionic acid halide and 3-methyl-3-butenylmagnesium halide. The octenoic acid [1] is treated with acetic anhydride under heat in the presence of an acidic catalyst to give 3,7-dimethyl-2,6-octadien-4-olide. The olide is reduced in an ordinary manner to give rosefuran.

6 Claims, No Drawings

METHOD FOR PRODUCING ROSEFURAN PRECURSOR AND INTERMEDIATES THEREFOR

FIELD OF THE INVENTION

The present invention relates to a precursor substance to be used for producing rosefuran, which is an important component for a rose-like fragrance, and also to a method for producing it.

BACKGROUND OF THE INVENTION

2-Alkyl-3-methylfurans have a peculiar fragrance, and many of them are useful in the fragrance-producing industry. For example, rosefuran of the following formula:

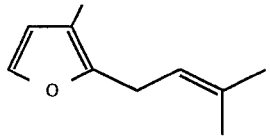

[3]

has a citrus-like fragrance and is known as an important minor component that forms a green top note of rose oil, and it is desired to establish an industrial method for producing it.

For synthetically producing rosefuran via 3,7-dimethyl-2,6-octadien-4-olide, there are known a method starting from 4-methyl-(5H)-furan-2-one and comprising introducing an alkyl side chain into the starting compound to give 3,7-dimethyl-2,6-octadien-4-olide (see D. R. Gedge, G. Pattenden; Tetrahedron Letters, 1977, 4443–4446) (hereinafter referred to as the first method),-and a method starting from methallyl alcohol and comprising seven steps of processing the starting compound for epoxidation, cyanation, etc. to give 3,7-dimethyl-2,6-octadien-4-olide (see S. Takano, M. Morimoto, S. Satoh, K. Ogasawara; Chemistry Letters, 1984, 1261–1262) (hereinafter referred to as the second method).

However, these methods are unsuitable in industrial use in that the first method produces structural isomers as side products while the separation and purification of the intended product from the isomers is difficult and that the second method must use tertiary-butyl peroxide, of which, however, the use of a large amount is dangerous, and requires many steps.

SUMMARY OF THE INVENTION

We, the present inventors have found that alkyl 3,7-dimethyl-4-oxo-7-octenoate, which is a novel compound and which is represented by a formula:

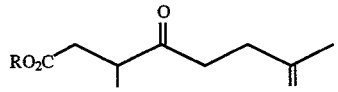

[1]

wherein R represents a lower alkyl group, is obtained in high yield by selective coupling reaction of 2-methyl-3-alkoxycarbonylpropionic acid halide and 3-methyl-3-butenylmagnesium halide (Grignard reagent), and additionally that, when the corresponding octenoic acid to be obtained by hydrolyzing the octenoate is treated with acetic anhydride in the presence of an acidic catalyst, the acid is unexpectedly cyclized and dehydrated favorably along with internal rearrangement of the terminal double bond, thereby easily giving 3,7-dimethyl-2,6-octadien-4-olide of a formula:

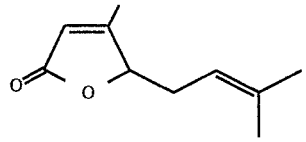

[2]

On the basis of these findings, we have completed the present invention. By reducing the olide compound in an ordinary manner, rosefuran is easily obtained.

Specifically, the present invention provides 3,7-dimethyl-4-oxo-7-octenoic acid and its esters of a formula:

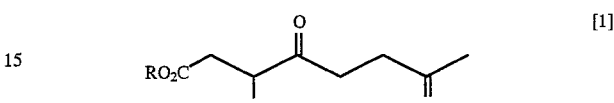

[1]

wherein R represents hydrogen or a lower alkyl group.

The present invention also provides a method for producing the compounds of formula [1] by reacting 2-methyl-3-alkoxycarbonylpropionic acid halide with 3-methyl-3-butenylmagnesium halide.

The present invention also provides a method for producing 3,7-dimethyl-2,6-octadien-4-olide of formula [2] by treating 3,7-dimethyl-4-oxo-7-octenoic acid of formula [1] with acetic anhydride under heat in the presence of an acid catalyst.

DETAILED DESCRIPTION OF THE INVENTION

The Grignard reaction in the present invention where 2-methyl-3-alkoxycarbonylpropionic acid halide is coupled with 3-methyl-3-butenylmagnesium halide to give alkyl 3,7-dimethyl-4-oxo-7-octenoate is effected by gradually and dropwise adding a solution of 3-methyl-3-butenylmagnesium halide to a solution of 2-methyl-3-alkoxycarbonylpropionic acid halide as dissolved in an organic solvent, in the presence of a copper salt catalyst and at a temperature between −50° C. and 0° C.

As the copper salt catalyst, favorably used is copper chloride, copper bromide or copper iodide. The amount of the catalyst to be used is from 0.005 to 0.05 equivalents, preferably from 0.01 to 0.03 equivalents, relative to the substrate halide.

The organic solvent to be used in the reaction may be any ordinary one that is generally used in ordinary Grignard reaction. Any of ether, tetrahydrofuran, benzene, toluene, xylene and others can be used, but toluene is especially preferred in the present invention.

As the halides, in general, the chlorides and the bromides are advantageously used. The alkoxycarbonyl group in the substrate, 2-methyl-3-alkoxycarbonylpropionic acid halide to be used in the present invention is a lower alkoxycarbonyl group such as methoxy, ethoxy, propoxycarbonyl or the like group.

According to the method of the present invention, the side reaction of the ester group in the starting acid halide or the carbonyl group in the product with the Grignard reagent is inhibited while only the desired coupling reaction of the acid halide with the Grignard reagent is selectively promoted to give the intended alkyl 3,7-dimethyl-4-oxo-7-octenoate (formula 1) in high yield.

Next, the thus-obtained alkyl 3,7-dimethyl-4-oxo-7-octenoate is heated in an aqueous alkaline solution or an alkaline alcohol to obtain the corresponding novel compound, keto-acid or, namely, 3,7-dimethyl-4-oxo-7-octenoic acid.

The thus-obtained 3,7-dimethyl-4-oxo-7-octenoic acid is then dissolved in a solvent and an equivalent amount or a somewhat excessive amount of acetic anhydride is added thereto and heated under reflux in the presence of an acid catalyst, whereby the acid is cyclized and dehydrated along with isomerization of the terminal double bond to give 3,7-dimethyl-2,6-octadien-4-olide. As the solvent in this process, usable is a hydrocarbon solvent such as pentane, hexane, heptane, benzene, toluene, xylene or the like. Especially preferred is toluene. As the acid catalyst, usable is an organic acid such as acetic acid, para-toluene-sulfonic acid, camphor-sulfonic acid or the like.

Rosefuran is produced from 3,7-dimethyl-2,6-octadien-4-olide obtained above in an ordinary manner by dissolving the olide in pentane or toluene followed by reducing it with diisobutylaluminium hydride as gradually added thereto at low temperatures.

The present invention is described in more detail by means of the following examples, which, however, are not intended to restrict the scope of the present invention.

Example 1

Preparation of methyl 3,7-dimethyl-4-oxo-7-octenoate (Compound of formula [1])

2-Methyl-3-methoxycarbonylpropionic acid chloride (150 g) was dissolved in toluene (700 ml), and copper bromide (1.4 g) was added thereto and cooled to −30° C. To the solution was gradually and dropwise (over a period of one hour) added a solution of 3-methyl-3-butenylmagnesium chloride in tetrahydrofuran (900 ml) as prepared from 3-methyl-3-butenyl chloride (95.3 g) and magnesium (24.3 g). The resulting reaction mixture was stirred for further one hour at the same temperature, and then 5% hydrochloric acid (500 ml) was gradually added thereto by which the reaction was stopped and the reaction mixture was restored to its room temperature condition. The resulting toluene layer was washed with saturated brine (500 ml), saturated aqueous sodium hydrogencarbonate (500 ml) and saturated brine (500 ml, twice), and thereafter dried over magnesium sulfate. The magnesium sulfate was removed by filtration, and then toluene was removed by distillation under reduced pressure. Thus was obtained a crude, liquid reaction product (177 g). By distilling the product, obtained was a colorless, transparent oily substance (147 g, b.p. 110°–120° C./8 mmHg). Its gas chromatographic analysis revealed that the essential component of the substance had a purity of 91%. A part of this was isolated and purified by silica gel chromatography using n-hexane-ethyl acetate (9:1), and it was identified as a novel compound, methyl 3,7-dimethyl-4-oxo-7-octenoate from the following analytical values:

IR (KBr) $v_{cm}^{-1}$: 1720 (ketone C=O), 1745 (ester C=O) $^1$H-NMR (60 MHz, CDCl$_3$) $\delta_{ppm}$: 1.10–1.22 (d, —CH$_3$, 3H), 1.75 (s, —CH$_3$, 3H), 2.08–3.35 (m, —CH$_2$X3, —CH, 7H), 3.62 (s, —OCH$_3$, 3H), 4.69–4.85 (m, =CH$_2$, 2H)

Example 2

Preparation of 3,7-dimethyl-4-oxo-7-octenoic acid

Methyl 3,7-dimethyl-4-oxo-7-octenoate (146 g) was dissolved in a solution of potassium hydroxide (63 g) in methanol (500 ml) and heated under reflux for one hour. After cooled, the non-reacted substances were removed by extraction with ether, and the remaining liquid was made acidic (at pH 2) with 10% hydrochloric acid. Next, the thus-separated oily component was extracted with ether (300 ml), then washed with saturated brine (200 ml) and then dried over magnesium sulfate. The magnesium sulfate was removed by filtration, and the ether was removed by distillation under reduced pressure. Thus was obtained a colorless, transparent oily substance (116 g). Its gas chromatographic analysis revealed that the essential component of the substance had a purity of 94%. This was identified as a novel compound, 3,7-dimethyl-4-oxo-7-octenoic acid from the following analytical values:

IR (KBr) $v_{cm}^{-1}$: 3200 (OH), 1720 (acid C=O+ketone C=O) $^1$H-NMR (60 MHz, CDCl$_3$) $\delta_{ppm}$: 0.95–1.08 (d, —CH$_3$, 3H), 1.58 (d, —CH$_3$, 3H), 2.00–3.13 (m, —CH$_2$X3, —CH, 7H), 4.45–4.68 (m, =CH$_2$, 2H), 7.23–7.55 (broad, s, OH, 1H)

Example 3

Preparation of 3,7-dimethyl-2,6-octadien-4-olide (Compound of formula [2])

3,7-Dimethyl-4-oxo-7-octenoic acid (115 g) was dissolved in toluene (650 ml), and acetic anhydride (133 g) and para-toluene-sulfonic acid (2 g) were added thereto and heated under reflux for 2 hours. Next, toluene (about 300 ml) was removed by distillation under ordinary pressure, and the remaining liquid was cooled to room temperature. Then, this was washed with saturated brine (300 ml), saturated aqueous sodium hydrogencarbonate (300 ml) and saturated brine (300 ml, twice), and thereafter dried over magnesium sulfate. The magnesium sulfate was removed by filtration, and then toluene was removed by distillation under reduced pressure. Thus was obtained a brown oily substance (121 g). This was subjected to simple distillation under reduced pressure to obtain an yellow oily fraction (96.4 g). The fraction was further subjected to precision distillation to obtain a pale yellow oily substance (53.5 g). This was analyzed to give the following data, which correspond to the data of 3,7-dimethyl-2,6-octadien-4-olide as described in literature (Japanese Patent Laid-Open No. 61-65877).

Boiling point: 110°–116° C./2 mmHg IR (KBr) $v_{cm}^{-1}$: 1768 (C=O) $^1$H-NMR (60 MHz, CDCl$_3$) $\delta_{ppm}$: 1.65 (s, —CH$_3$, 3H), 1.71 (s, —CH$_3$, 3H), 2.05 (s, —CH$_3$, 3H), 2.20–2.72 (m, —CH$_2$—, 2H), 4.68–5.21 (m, —CH, —CH=, 2H), 5.67–5.85 (bs, —CH=, 1H)

Referential Example

Preparation of Rosefuran 3,7-Dimethyl-2,6-octadien-4-olide (80 g) was dissolved in pentane (670 ml) and cooled to −30° C. in an argon atmosphere. Next, a solution of diisobutylaluminium hydride (0.93 mol/liter) in n-hexane (520 ml) was gradually and dropwise (over a period of 2 hours) added thereto. The reaction mixture was stirred for one hour at the same temperature and then poured into 5% hydrochloric acid with ice (600 ml). The thus-separated pentane layer was washed with saturated brine (500 ml), saturated aqueous sodium hydrogencarbonate (300 ml) and saturated brine (300 ml, twice), and thereafter dried over magnesium sulfate. The magnesium sulfate was removed by filtration and pentane was removed by distillation under ordinary pressure. Thus was obtained a colorless oily substance (73.4 g). This was subjected to simple distillation under reduced pressure to obtain a colorless oily fraction (42.5 g). This exhibited a purity of 99% through its gas chromatographic analysis, while giving the following data which well correspond to the data of rosefuran as described in literature (B. M. Trost and J. A. Flygare; J. Org. Chem., 1994, 59, 1078–1082).

Boiling point: 99°–101° C./30 mmHg $^1$H-NMR (60 MHz, CDCl$_3$) $\delta_{ppm}$: 1.72 (s, —CH$_3$X2, 6H), 1.96 (s, —CH$_3$, 3H), 3.25–3.37 (d, —CH$_2$—, 2H), 5.08–5.45 (m, —CH=, 1H), 7.21–7.24 (d, OCH=, 1H)

According to the present invention, it is possible to produce a novel compound of formula [1] in high yield from acid halide and Grignard reagent, both of which are easily available, without producing any other side products. From this novel compound, obtainable is 3,7-dimethyl-2,6-octadien-4-olide having a high purity. By reducing the olide in an ordinary manner, obtained is rosefuran. Thus, the present invention has realized the industrial mass-production of rosefuran from the novel compound of formula [1], without requiring any complicated steps.

While the invention has been described in detail and with reference to specific embodiments thereof, it will be apparent to one skilled in the art that various changes and modifications can be made therein without departing from the spirit and scope thereof.

What is claimed is:

1. 3,7-Dimethyl-4-oxo-7-octenoic acid and its esters of a formula:

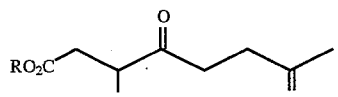

[1]

wherein R represents hydrogen or a lower alkyl group.

2. Compound as claimed in claim 1, wherein R is methyl.
3. A method for producing compounds of a formula:

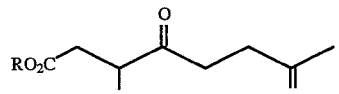

[1]

wherein R represents hydrogen or a lower alkyl group, comprising reacting 2-methyl-3-alkoxycarbonylpropionic acid halide with 3-methyl-3-butenylmagnesium halide.

4. The method as claimed in claim 3, wherein a copper salt catalyst is added to the reaction system.

5. A method for producing 3,7-dimethyl-2,6-octadien-4-olide of a formula:

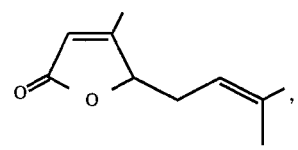

[2]

comprising treating 3,7-dimethyl-4-oxo-7-octenoic acid of a formula:

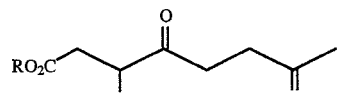

[1]

wherein R represents hydrogen, with acetic anhydride under heat in the presence of an acid catalyst.

6. A method for producing 3,7-dimethyl-2,6-octadien-4-olide of a formula:

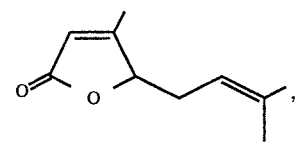

[2]

comprising obtaining methyl 3,7-dimethyl-4-oxo-7-octenoate of a formula:

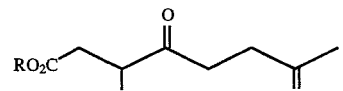

[1]

wherein R represents methyl, by coupling reaction of 2-methyl-3-methoxycarbonylpropionic acid chloride with 3-methyl-3-butenylmagnesium chloride (Grignard reagent), then hydrolyzing the resulting keto-ester into 3,7-dimethyl-4-oxo-7-octenoic acid and thereafter subjecting the resulting acid to cyclization and dehydration along with rearrangement of the double bond in the molecule.

* * * * *